United States Patent [19]

Prasad et al.

[11] Patent Number: 5,792,872
[45] Date of Patent: Aug. 11, 1998

[54] PROCESS FOR PRODUCING N-(4-FLUOROPHENYL)-N-(1-METHYLETHYL)-2-[(5-TRIFLUOROMETHYL-1,3,4-THIADIAZOL-2-YL)OXY]ACETAMIDE

[75] Inventors: Vidyanatha A. Prasad, Leawood, Kans.; Jacqueline M. Applegate, Parkville; Daniel M. Wasleski, Raytown, both of Mo.; Klaus Jelich, Overland Park, Kans.

[73] Assignee: Bayer Corporation, Pittsburgh, Pa.

[21] Appl. No.: 989,564

[22] Filed: Dec. 12, 1997

[51] Int. Cl.⁶ ................................................. C07D 285/13
[52] U.S. Cl. ................................................. 548/136
[58] Field of Search ................................. 548/136

[56] References Cited

U.S. PATENT DOCUMENTS

| | | |
|---|---|---|
| 4,585,471 | 4/1986 | Förster et al. ............ 71/90 |
| 4,645,525 | 2/1987 | Förster et al. ............ 71/88 |
| 4,756,741 | 7/1988 | Förster et al. ............ 71/90 |
| 4,968,342 | 11/1990 | Förster et al. ............ 71/90 |
| 5,090,991 | 2/1992 | Förster et al. ............ 71/90 |
| 5,101,034 | 3/1992 | Schmidt et al. ............ 548/136 |

*Primary Examiner*—Robert Gerstl
*Attorney, Agent, or Firm*—Joseph C. Gil; Carol Marmo

[57] ABSTRACT

The present invention relates to a process for making N-(4-fluorophenyl)-N-(1-methylethyl)-2-[(5-(trifluoromethyl)-1,3,4-thiadiazol-2-yl)oxy]acetamide, which process includes the steps of reacting 2-(methylsulfonyl)-5-(trifluoromethyl)-1,3,4,-thiadiazole with N-(4-fluorophenyl)-2-hydroxy-N(1-methylethyl) acetamide in an aprotic, aromatic solvent with aqueous alkali to form an aqueous phase and an organic phase, separating the aqueous and organic phases and recovering the N-(4-fluorophenyl)-N-(1-methylethyl)-2-[(5-(trifluoromethyl)-1,3,4-thiadiazol-2-yl)oxy]acetamide from the organic phase. A preferred solvent and aqueous alkali are toluene and aqueous sodium hydroxide, respectively.

10 Claims, No Drawings

PROCESS FOR PRODUCING N-(4-FLUOROPHENYL)-N-(1-METHYLETHYL)-2-[(5-TRIFLUOROMETHYL-1,3,4-THIADIAZOL-2-YL)OXY]ACETAMIDE

TECHNICAL FIELD OF THE INVENTION

The field of this invention is the synthesis of acetamide herbicides. More particularly, this invention relates to processes for producing N-(4fluorophenyl)-N-(1-methylethyl)-2-[(5-trifluoromethyl-1,3,4-thiadiazol-2yl)oxy]acetamide.

BACKGROUND OF THE INVENTION

Certain heteroaryloxy-carboxylic acid amides and heteroaryloxyacetamides of the general formula R-O-CH($R^1$)-CO-N($R^2$)($R^3$) are known to have herbicidal activity (See, e.g., U.S. Pat. Nos. 4,756,741 and 5,101,034). U.S. Pat. No. 5,101,034 discloses a particular class of heteroaryloxyacetamides, namely thiadiazole acetamides as having herbicidal activity. The thiadiazole acetamides are made by reacting a thiadiazole sulfone with a hydroxyacetanilide in acetone. Of particular relevance to the present invention is the disclosure of a synthetic scheme for making 2-(5-trifluoromethyl)-1,3,4thiadiazol-2-yl-oxy)-N-methylacetanilide. In accordance with that synthetic scheme, 2-methylsulfonyl-5-trifluoromethyl-1,3,4-thiadiazole is reacted with N-methyl-2-hydroxyacetanilide, potassium carbonate, and tetraethylammonium bromide. Acetone is used as the solvent for the reaction. The reaction is carried out at a temperature of 20° C.–25° C. for 20 hours. Undissolved salts are filtered off and washed with acetone. The filtrate is freed of solvent in vacuo and the resulting residue taken up in diethyl ether, washed with dilute hydrochloric acid, dried and filtered. After freeing the filtrate of solvent, the end product is crystallized from the oily residue. Reported yields are about 90%.

U.S. Pat. Nos. 4,756,741 and 4,645,525 disclose a synthetic scheme for making O-(2-trifluoromethyl-1,3,4,-thiadiazol-5-yl-oxy)acetic N-methylanilide. In accordance with that scheme, 2-hydroxyacetic acid-N-methylanilide is reacted with dimethylsulfoxide and calcium oxide at 50° C. for 1 hour. 5-Bromo-2-trifluoromethyl-1,3,4thiadiazole is then added to the reaction mixture and the mixture stirred at 50° C. for 40 hours. The mixture is then poured into water and the oil that precipitates is extracted with methylene chloride. The end product is obtained in about 90% yield by distilling off the methylene chloride.

U.S. Pat. No. 4,585,471 discloses synthetic schemes for making (5-trifluoromethyl-1,3,4-thiadiazol-2-yl-oxy)-acetic acid 2-ethylpiperidine and (5-trifluoromethyl-1,3,4-thiadiazol-2-yl-oxy)-acetic acid 2-methylpiperidine. In accordance with those synthetic schemes, the ethylpiperidine compound is made by reacting hydroxyacetic acid-2-ethylpiperidine with 2-chloro-5-trifluoromethyl-1,3,4-thiadiazole in the presence of potassium tert-butanate in tert-butanol at a temperature of 20° C. to 30° for 3 hours and the methylpiperidine compound is made by reacting 2-chloro-5-trifluoromethyl-1,3,4-thiadiazole in toluene with hydroxyacetic acid-2-methylpiperidine in the presence of sodium hydroxide. The end product, in both cases, is recovered from the reaction mixture by acidification with hydrochloric acid, drying, removal of solvent and crystallization. The reported yields of the end-products were 66% (ethylpiperidine) and 54% (methylpiperidine).

U.S. Pat. Nos. 4,968,342 and 5,090,991 disclose a synthetic scheme for making N-isopropyl-(5-trifluoromethyl-1,3,4,-thiadiazol-2-yl)-3-chlorooxyacetanilide. In accordance with that scheme, 2-methylsulfonyl-5-trifluoromethyl-1,3,4-thiadiazole, dissolved in acetone, is reacted with 3-chloro-N-isopropylhydroxyacetanilide in the presence of sodium hydroxide and water for 3 hours at –20° C. Water is added to the reaction mixture and the crystalline end-product is obtained by crystallization in 85% yield.

It can be seen from the above, that existing methods for making acetamide herbicides suffer from low yields (54% to 85%), prolonged reaction times (20 to 40 hours) or the use of problematic solvents (acetone). There continues to be a need in the art, therefore, for a practical method for making these herbicides, which method avoids the problems of the existing art.

BRIEF SUMMARY OF THE INVENTION

The present invention provides a process for making N-(4-fluorophenyl)-N-(1-methylethyl)-2-[(5-(trifluoromethyl)-1,3,4-thiadiazol-2-yl)oxy]acetamide. The process includes the steps of reacting 2-(methylsulfonyl)-5-(trifluoromethyl)-1,3,4,-thiadiazole with N-(4-fluorophenyl)-2-hydroxy-N(1-methylethyl)acetamide in the presence of an aprotic, aromatic solvent and an aqueous alkali to form an aqueous phase and an organic phase, separating the aqueous and organic phases and recovering the N-(4-fluorophenyl)-N-(1-methylethyl)-2-[(5-(trifluoromethyl)-1,3,4-thiadiazol-2-yl)oxy]acetamide from the organic phase.

Exemplary and preferred aprotic, aromatic solvents are toluene, cumene, xylene or mesitylene. Toluene is most preferred. The alkali is preferably an alkali metal hydroxide or alkali metal carbonate. A preferred alkali metal is sodium, potassium or lithium. A preferred alkali metal hydroxide is sodium hydroxide.

The pH of the aqueous phase is from about 11 to about 14, preferably from about 12 to about 14. N-(4-fluorophenyl)-N-(1-methylethyl)-2-[(5-(trifluoromethyl-1,3,4-thiadiazol-2-yl)oxy]acetamide is recovered from the organic phase by acidifying the organic phase after separation from the aqueous phase and removing the solvent from the acidified organic phase.

DETAILED DESCRIPTION OF THE INVENTION

I. The Invention

The present invention relates to processes for the synthesis, recovery and isolation of the herbicide, N-(4-fluorophenyl)-N-(1-methylethyl)-2-[(5-trifluoromethyl-1,3,4-thiadiazol-2-yl oxy]acetamide. The synthetic process includes the step of reacting 2-(methylsulfonyl)-5-(trifluoromethyl)-1,3,4-thiadiazole with N-(4-fluorophenyl)-2-hydroxy-N-(1-methylethyl)acetamide in an aprotic, aromatic solvent. Formed N-(4-fluorophenyl)-N-(1-methylethyl)-2-[(5-trifluoromethyl-1,3,4-thiadiazol-2yl)oxy]acetamide can be recovered via phase separation followed by acidification of the organic phase. By following such a protocol it is also possible to use a lower quality TDA Sulfone because the impurities therein are retained in the alkaline aqueous phase. Also, because most of the by-products of the reaction are acidic in nature, they remains in the alkaline aqueous phase. Isolation is accomplished by removal of the solvent and flaking of the molten residue.

II. Method of Making N-(4-fluorophenyl)-N-(1-methylethyl)-2-[(5-trifluoromethyl-1,3,4-thiadiazol-2-yl)oxy]acetamide Using an Aprotic, Aromatic Solvent The process for making N-(4-fluorophenyl)-N-(1-methylethyl)-2-[(5-trifluoromethyl-1,3,4-thiadiazol-2-yl)oxy]acetamide includes the step of reacting 2-(methylsulfonyl)-5-(trifluoromethyl)-1,3,4-thiadiazole with N-(4-fluorophenyl)-2-hydroxy-N-(1-methylethyl) acetamide in an aprotic, aromatic solvent. The solvent is preferably toluene, xylene, cumene or mesitylene and, most preferably toluene.

The 2-(methylsulfonyl)-5-(trifluoromethyl)-1,3,4-thiadiazole (TDA sulfone) and the N-(4-fluorophenyl)-2-hydroxy-N-(1-methylethyl)-acetamide (FOE hydroxy) used in the present process can be made using any method. Preferably the two reactants are prepared using a method that results in the reactants being dissolved in the aprotic, aromatic solvent used in the present process. Some processes for making TDA sulfone can be found in United States Patent Applications entitled "Synthesis of 2-(Methylsulfonyl)-5-(Trifluoromethyl)-1,3,4-Thiadiazole Using Oxidation of 2-(Methylthio)-5-(Trifluoromethyl)-1,3, 4-Thiadiazole with a Molybdenum or Tungsten Catalyst", and "Synthesis of 2-(Methylsulfonyl)-5-(Trifluoromethyl)-1,3,4- Thiadiazole Using Oxidation of 2-(Methylthio)-5-(Trifluoromethyl)--1,3,4-Thiadiazole with Acetic Acid", filed concurrently herewith. Preferred means for making FOE hydroxy can be found in United States Patent Applications entitled "Conversion of N-(4-fluorophenyl)-2-Hydroxy-N-(1-Methylethyl) Acetamide Acetate to N-(4-fluorophenyl)-2-Hydroxy-N-(1-methylethyl Acetamide" and "Method of Making N-(4-Fluorophenyl)-2-Hydroxy-N-(1-Methylethyl) Acetamide Using Sodium Formate," filed concurrently herewith. The disclosures of all four of these patent applications are incorporated herein by reference. The molar ratio of 2-(methylsulfonyl)-5-(trifluoromethyl)-1,3,4-thiadiazole to N-(4-fluorophenyl)-2-hydroxy-N-(1-methlethyl)acetamide is from about 1.5:1 to about 1:1.5 and more preferably about 1:1.

Where the TDA sulfone and FOE hydroxy are not provided in the solvent, the solvent is added to the reaction mixture. The molar ratio of solvent (e. g., toluene) to either TDA sulfone or FOE hydroxy is from about 1:1 to about 5:1. The solvent is preferably present in a molar excess relative to TDA sulfone and FOE hydroxy.

The reaction of TDA sulfone and FOE hydroxy typically occurs at a relatively cool temperature. Preferably the reaction temperature is from about −10° C. to about 30° C. More preferably, the temperature is from about −5° C. to about 15° C. and, most preferably from about 0° C. to about 10° C.

In a preferred embodiment, the reaction occurs in the presence of an aqueous alkali. Exemplary and preferred aqueous alkalis are aqueous alkali metal hydroxides or carbonates. Alkali metal hydroxides and carbonates are well known in the art. Exemplary and preferred alkali metals are potassium, sodium and lithium. Sodium is most preferred. The molar ratio of the aqueous alkali (e. g., sodium hydroxide) to the primary reactants (e. g., TDA sulfone and FOE hydroxy) is from about 1:1 to about 2:1 and, preferably from about 1.25:1 to about 1.75:1. The aqueous alkali is added to the reaction mixture as an aqueous solution of the hydroxide or carbonate. Preferably the alkali metal hydroxide or carbonate concentration of the solution is from about 15 weight percent to about 60 weight percent. More preferably, the concentration is from about 15 weight percent to about 50 weight percent.

The aqueous alkali can be added at a single time or added in portions over a prolonged period of time. The mixture of TDA sulfone and FOE hydroxy is agitated during the entire time over which the alkali is added. A sufficient amount of alkali is used so as to maintain the pH of the reaction mixture at a pH value of from about 10 to about 14.

In an especially preferred embodiment, the process includes the steps of adding 2-(methylsulfonyl)-5-(trifluoromethyl)-1,3,4-thiadiazole in toluene and N-(4-fluorophenyl)-2-hydroxy-N-(1-methylethyl)acetamide in toluene to a reaction vessel to form a reaction mixture, cooling the reaction mixture to about 0° C.–5° C., adding an aqueous solution of sodium hydroxide to the reaction mixture slowly over 0 to 3 hours and maintaining the reaction mixture at a temperature of from about 0° C. to about 5° C. for a period of time ranging from about 0 hour to about 3 hours.

The process can further include the step of recovering the N-(4-fluorophenyl)-N-(1-methylethyl)-2-[(5-trifluoromethyl-1,3,4-thiadiazol-2-yl)oxy] acetamide. Recovery can be accomplished using any well known recovery method. Recovery is accomplished as set forth below.

III. Recovery of N-(4-fluorophenyl)-N-(1-methylethyl)-2-[(5-trifluoromethyl-1,3,4-thiadiazole-2-yl)oxy]acetamide via Acidification After Phase Separation In another aspect, the present invention provides a process for recovering N-(4-fluorophenyl)-N-(1-methylethyl)-2-[(5-trifluoromethyl-1,3,4-thiadiazol-2-yl)oxy]acetamide from a reaction mixture. The recovery process can be used to recover N-(4-fluorophenyl)-N-(1-methylethyl)-2-[(5-trifluoromethyl)-1,3,4-thiadiazol-2-yl)oxy]acetamide produced by any means. However formed, the present recovery process begins with N-(4-fluorophenyl)-N-(4-methylethyl)-2-[(5-trifluoromethyl-1,3,4-thiadiazol-2-yl)oxy]acetamide dissolved or suspended in a reaction mixture having an organic phase ( e.g., an aprotic, aromatic solvent such as toluene) and an alkaline aqueous phase. In a preferred embodiment, N-(4-fluorophenyl)-N-( 1-methylethyl)-2-[(5-trifluoromethyl-1 ,3,4-thiadiazol-2-yl)oxy]acetamide is made by the process of Section II. above.

The aqueous and organic phases are separated and the N-(4-fluorophenyl)-N-(4-methylethyl)-2-[(5-trifluoromethyl-1,3,4-thiadiazol-2-yl)oxy]acetamide is recovered from the organic phase. The organic phase containing the N-(4-fluorophenyl)-N-(1-methylethyl)-2-[(5-trifluoromethyl-1,3,4-thiadiazol-2-yl)oxy]acetamide is acidified prior to removal of solvent. Acidification is accomplished by adding an acid to the organic phase. Suitable acids, for example, are hydrochloric acid, nitric acid and sulfuric acid. Sulfuric acid is preferred.

N-(4-fluorophenyl)-N-(1-methylethyl)-2-[(5-trifluoromethyl-1,3,4-thiadiazol-2-yl)oxy]acetamide can be recovered from the acidified organic phase using any means well known in the art. Exemplary such means include crystallization, flaking and filtration after removal of solvent. A preferred means of isolation is flaking as described below. As set forth hereinafter in the Examples, recovery using acidification results in yields of greater than about 90%.

In an especially preferred embodiment, N-(4-fluorophenyl)-N-(1-methylethyl)-2-[(5-trifluoromethyl)-1, 3,4-thiadiazol-2-yl)oxy]acetamide is made and recovered according to a process that includes the steps of adding 2-(methylsulfonyl)-5-(trifluoromethyl)-1,3,4-thiadiazole in toluene and N-(4-fluorophenyl)-2-hydroxy-N-(1-methylethyl)acetamide in toluene to a reaction vessel to form a reaction mixture, cooling the reaction mixture to about 0° C.–5° C., adding an aqueous solution of sodium hydroxide to the reaction mixture and maintaining the reaction mixture at a temperature of from about 0° C. to about 15° C. for a period of time ranging from about 0 to about 3 hours to form a reaction product having an aqueous and an organic phase, separating the aqueous and organic phases, adding sulfuric acid to the organic phase and recovering the N-(4-fluorophenyl)-N-(1-methylethyl)-2-[(5- trifluoromethyl-1,3,4-thiadiazol-2-yl)oxy]acetamide from the organic phase.

IV. Isolation of N-(4-fluorophenyl)-N-(1-methylethyl)-2-[(5-trifluoromethyl-1,3,4-thiadiazole-2-yl)oxy]acetamide via Flaking In another aspect, the present invention provides a process for isolating N-(4-fluorophenyl)-N-(1-methylethyl)-2-[(5-trifluoromethyl-1,3,4-thiadiazol-2-yl)oxy]acetamide. In accordance with this process, N-(4-fluorophenyl)-N-(1-methylethyl)-2-[(5-trifluoromethyl-1,3,4-thiadiazol-2-yl)oxy]acetamide, obtained by any means, is in a solvent such as toluene. The solvent is removed via evaporation and the solid product isolated from its molten form via a flaking operation. As used herein, the term "flaking" means, as is well known in the art, solidification or crystallization.

Solvent can be removed from the solution using any means well known in the art. A preferred means of solvent removal is vacuum or steam distillation. The molten material is then spread out in a thin layer on a solid surface, cooled to a temperature of from about 20° C. to about 30° C. (room temperature) and maintained at that temperature until crystallization. The product crystallizes as aggregates of flakes on the solid surface.

The Examples to follow illustrate preferred embodiments of the present invention and are not limiting of the claims and specification in any way.

EXAMPLE 1

Synthesis of N-(4-Fluoropenyl)-N-(1-Methylethyl)-2-[(5-trifluoromethyl-1,3,4-thiadiazol-2-yl)oxy]acetamide(Fluthiamide).

FOE Hydroxy (FOEH), TDA sulfone (TDAS) and toluene were added to a reaction vessel. NaOH was slowly added over time to the vessel. The reaction mixture was agitated over a period of time. The reaction conditions are set forth below.

| Toluene/FOEH Mole Ratio | 5.90–6.60 |
|---|---|
| TDAS/FOEH Mole Ratio | 1.00–1.15 |
| NaOH/FOEH Mole Ratio | 1.00–1.75 |
| NaOH Concentration (wt. percent) | 15–60 |
| NaOH Add Time | 1–3 hours |
| Reaction Temperature | −10 to 30° C. |
| Reaction Time | 0–3 hours |

EXAMPLE 2

Recovery of Fluthiamide

After the primary reaction (see Example 1), the temperature was adjusted to the desired level. Three phases were formed: a bottom phase—NaOH aqueous (discarded); a middle phase—rag (retained for treatment); and a top phase—Fluthiamide in toluene. The phases were separated in accordance with the conditions summarized as follows.

The rag phase was retained for further treatment as set forth below. Process water and sulfuric acid were charged to this phase to reduce the pH. The resulting acidified mixture was heated to the desired temperature and filtered at that temperature. The phase separation conditions are summarized as follows.

| $H_2O$/Rag Wt. Ratio | 0.50–1.50 |
|---|---|
| Phase Separation pH | 1.0–4.0 |
| Phase Separation Temp | 50–70° C. |

Sulfuric acid (70% weight) was added to the Fluthiamide/Toluene, phase to reduce the pH of that phase to 1.5. This acidified phase was retained for Fluthiamide isolation. Fluthiamide was isolated using two different methods (Examples 3 and 4). The amount of the rag can be decreased by using lower temperatures.

EXAMPLE 3

Isolation of Fluthiamide via Solidification

The organic phase from Example 2 was used for isolation of Fluthiamide. Toluene was removed by an atmospheric steam strip. After removal of the toluene, the Fluthiamide was left in a molten Fluthiamide/aqueous phase mixture. The aqueous phase was removed and the Fluthiamide was obtained by solidification of the organic phase. When this isolation method was used, the Fluthiamide was produced with an average purity of 96.2%.

EXAMPLE 4

Synthesis of Fluthiamide.

A 2 liter, 4-necked round bottom flask containing 632.2 g of a TDA-sulfone suspension in toluene (1.0M of ca. 99% A.I. TDA-sulfone, on a solvent-free basis) was fitted with an overhead stirrer, thermometer, 250 ml barostatic addition funnel and a dry ice acetone bath. The toluene TDA-sulfone slurry was cooled to 0° C. with agitation. 415.7 g of a FOE-hydroxy solution in toluene (1.0M of ca. 98% A.I. FOE-hydroxy on a solvent-free basis) was added to the TDA-sulfone slurry in toluene with agitation at 0°–5° C. The amount of toluene required for the reaction can be reduced by about 50% if solid TDA-sulfone is used instead of a TDA-sulfone suspension in toluene.

A 25% NaOH solution was added to the reaction mixture over a period of 1 to 5 hours at 0° to 5° C. under constant agitation. The addition of NaOH can be done over various times without adverse results. The entire mixture was cooked for 1 hr at 0°–5° C.

The mixture was transferred to a separatory funnel and the phases were separated at 0°–10° C. The aqueous phase was extracted with two portions of toluene (about 50 g each portion). The organic phases were all combined and treated with about 1 g of conc. HCl or 1 g of conc. $H_2SO_4$ (pH 4.5). The solvent toluene was stripped by means of a rotary evaporator under water aspirator vacuum (ca. 20 mm Hg) using a maximum bath temperature of 80° C. The molten product was poured onto an enamel pan and allowed to flake. The flaked material was crushed and dried under vacuum at ambient temperature. Fluthiamide was produced with a purity of 98.2% and a net yield (N.Y.) of 93.2%, based on TDA-Sulfone.

In additional studies, the effects of reaction temperature and FOE-hydroxy purify on fluthiamide production were tested. The procedures used were the same as set forth above. The results of these studies are summarized in the tables, below:

| Exper # | Rxn Temp (°C.) | Fluthiamide A.I. (%) | Net Yield based on FOE-Chloride (%) |
|---|---|---|---|
| 1 | 0–5 | 98.2 | 95.5 |
| 2 | 5–10 | 98 | 95.1 |
| 3 | 10–15 | 98.1 | 94.7 |
| 4 | 15–20 | 97.8 | 94 |
| 4 | 20–30 | 96.8 | 93.6 |

It can be seen from the data in the table, above, that fluthiamide purity and net yield decreased with increasing reaction temperatures over the range of ° C. to 30° C.

| Exper # | FOE-Hydroxy A.I. (%) | Fluthiamide A.I. (%) | Net Yield based on FOE-Chloride* (%) |
|---|---|---|---|
| 1 | 98.2 | 98.2 | 95.5 |
| 2 | 97.3 | 96.8 | 94.8 |
| 3 | 96.4 | 95.5 | 93.5 |
| 4 | 95.2 | 95.1 | 93.4 |
| 5 | 94.8 | 94.3 | 93.2 |

*FOE Chloride is the precursor to FOE-Hydroxy

The data in the table above shows that fluthiamide purity and yield are directly proportional to the purity of FOE-hydroxy used in the reaction.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making N-(4-fluorophenyl)-N-(1-methylethyl)2-[(5-(trifluoromethyl-1,3,4-thiadiazol-2-yl)oxy]acetamide comprising reacting 2-(methylsulfonyl)-5-(trifluoromethyl)-1,3,4,-thiadiazole with N-(4fluorophenyl)-2-hydroxy-N(1-methylethyl)aceamide in the presence of an aqueous alkali and an aprotic, aromatic solvent to form an aqueous phase and an organic phase, separating the aqueous and organic phases and isolating the N-(4-fluorophenyl)-N-(1-methylethyl)-2-[(5(trifluoromethyl-1,3,4-thiadiazol-2-yl)oxy]acetamide from the organic phase.

2. The process of claim 1 wherein the aprotic, aromatic solvent is toluene, cumene, xylene or mesitylene.

3. The process of claim 2 wherein the solvent is toluene.

4. The process of claim 1 wherein the aqueous alkali is an aqueous alkali metal hydroxide or an aqueous alkali metal carbonate.

5. The process of claim 4 wherein the alkali metal is sodium, potassium or lithium.

6. The process of claim 5 wherein the alkali metal hydroxide is sodium hydroxide.

7. The process of claim 1 wherein the aqueous alkali is an aqueous solution of from about 15 weight percent to about 50 weight percent sodium hydroxide.

8. The process of claim 1 wherein the reaction mixture has a pH value of from about 8 to about 14.

9. The process of claim 1 further comprising the step of acidification of the organic phase after separation from the aqueous phase.

10. The process of claim 1 wherein recovery is performed by removing the solvent from the acidified organic phase followed by solidification of the molten product.

* * * * *